United States Patent [19]

Fahey et al.

[11] Patent Number: 4,803,163

[45] Date of Patent: Feb. 7, 1989

[54] PREPARATION OF A PROTEIN FRACTION EXHIBITING CELL GROWTH-INHIBITING ACTIVITY

[75] Inventors: Diana Fahey; Ernest Knight, Jr., both of Wilmington, Del.

[73] Assignee: E. I. Du Pont de Nemours and Company, Wilmington, Del.

[21] Appl. No.: 883,742

[22] Filed: Jul. 9, 1986

Related U.S. Application Data

[63] Continuation-in-part of Ser. No. 617,073, Jun. 4, 1984, abandoned.

[51] Int. Cl.[4] ............................................. C12P 21/00
[52] U.S. Cl. .................................. 435/68; 435/240.2; 435/948; 530/351
[58] Field of Search .......................... 435/68; 530/351

[56] References Cited

U.S. PATENT DOCUMENTS

| 4,172,071 | 10/1979 | DeMaeyer et al. | 424/85 |
| 4,225,670 | 9/1980 | Tolbert et al. | 435/68 |
| 4,278,661 | 7/1981 | Knight | 424/85 |
| 4,343,736 | 8/1982 | Uemura et al. | 435/68 |
| 4,376,821 | 3/1983 | Braude | 435/68 |
| 4,376,822 | 3/1983 | Braude | 435/68 |
| 4,460,685 | 7/1984 | Vilcek | 435/70 |

OTHER PUBLICATIONS

Knight, E., *Proc. Nat. Acad. Sci. USA*, 73(2), 520–523 (1976).

*Primary Examiner*—Richard A. Schwartz

[57] ABSTRACT

A protein fraction isolated from tissue cultures of human diploid fibroblasts or lymphoblastoid cells inhibits the growth of heterologous human cells.

12 Claims, No Drawings

PREPARATION OF A PROTEIN FRACTION EXHIBITING CELL GROWTH-INHIBITING ACTIVITY

RELATED APPLICATION

This application is a continuation-in-part of U.S. Ser. No. 617,073, filed June 4, 1984, now abandoned.

BACKGROUND OF THE INVENTION

This invention relates to a process for preparing a protein fraction comprising proteins secreted by human cells. The secreted proteins inhibit growth of heterologous human cells. The invention also relates to the protein fraction which is a product of the process.

Numerous stimulators of cell growth are secreted by mammalian cells, but only a few substances capable of inhibiting cell growth are known. For example, interferon preparations reversibly inhibit multiplication of conspecific, homologous cells in cell culture. Paucker et al., *Virology* 17: 324 (1962), and Gresser et al., *Nature* 239: 167 (1972), report experiments in which these growth-inhibiting effects were observed. Apart from interferons, only a few proteins or protein mixtures with capacity to inhibit normal or neoplastic cell growth have been described.

For example, Redding et al., *Proc. Natl. Acad. Sci. USA* 79: 7014 (1982), describe isolation of a purified fraction from porcine hypothalami. This fraction displayed antimitogenic activity when introduced to growing cultures of certain normal and neoplastic cell lines. Loss of antimitogenic activity following exposure of the purified fraction to proteases indicated that the activity was probably associated with one or more polypeptides.

Kinders et al., *Biochem. J.* 190: 605 (1980), observed that certain glycopeptides isolated from cell surfaces of mouse cerebral cortex inhibited growth of baby hamster kidney cells. Burzynski et al., *Physiol. Chem. Phys.* 8: 13 (1976), isolated medium-sized peptides from human urine which inhibited DNA synthesis and mitosis in certain human neoplastic cell lines.

Sloane, U.S. Pat. No. 4,359,415, discloses a process for preparing a glycoprotein fraction from human urine containing a glycoprotein exhibiting antineoplastic activity.

Holley et al., *Proc. Natl. Acad. Sci. USA* 77: 5989 (1980), describe isolation of two high molecular weight growth inhibitors from cultures of monkey epithelial kidney cells. These substances selectively and reversibly inhibited growth of the cells from which they were derived.

McMahon et al., *Proc. Natl. Acad. Sci. USA* 79: 456 (1982), disclose purification of an inhibitor of cell proliferation from cultures of nonmalignant rat hepatic epithelial cells. This substance, which was determined to have a molecular weight of approximately 26,000 daltons, inhibited growth of nonmalignant rat liver cells in culture, but did not affect growth of malignant rat liver cells.

Endogenous substances capable of inhibiting growth of mammalian cells are of interest as potential therapeutic agents.

SUMMARY OF THE INVENTION

In accordance with the present invention, a process is provided for preparing a protein fraction comprising proteins which are capable of inhibiting the growth of human lymphoblastoid cells. The process comprises:

(a) growing human diploid fibroblast or lymphoblastoid cells in a culture medium under conditions which induce the cells to secrete proteins into the culture medium;

(b) contacting the culture medium with an immobilized triazinyl dye capable of binding human fibroblast or lymphoblastoid interferons, whereby bound and unbound protein fractions are formed; and (c) isolating the unbound protein fraction which contains the growth-inhibiting proteins.

DETAILED DESCRIPTION OF THE INVENTION

Human fibroblast interferon (interferon-$\beta$) is routinely prepared from human diploid fibroblast cells grown in monolayer culture by treating such cells with an interferon inducer, preferably a mixture of polyinosinic and polycytidylic acids (polyribo I: polyribo C) as disclosed by Havell et al., *Antimicrob. Agents Chemother.* 2: 476 (1972).

Alternatively, human lymphoblastoid cells capable of growth in suspension culture can be induced to secrete interferons and other proteins into culture media by treating the cells with either phorbol 12-myristate 13-acetate (PMA) or mezerein. The structure of mezerein appears below:

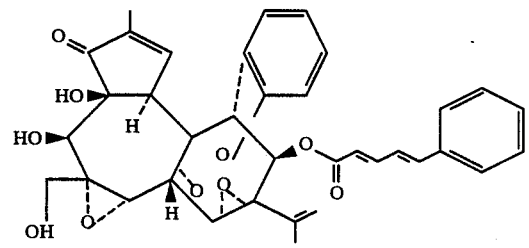

To purify interferon-$\beta$, culture medium containing secreted proteins is contacted with an immobilized triazinyl dye capable of binding human fibroblast or lymphoblastoid interferons, for example the blue dye marketed under the trademark Cibacron® Blue F3G-A. Certain proteins present in the culture medium, particularly interferon-$\beta$, bind tightly to the dye ligand. After separation of bound material from the remaining components of the medium, interferon-$\beta$ can be released from the dye ligand, achieving significant purification. This process is described in detail by De Maeyer et al., U.S. Pat. No. 4,172,071, and Knight, U.S. Pat. No. 4,278,661.

Typically, the foregoing process is conducted by passing fibroblast or lymphoblastoid culture medium through a column packed with cross-linked agarose covalently attached to the dye-ligand. Blue Sepharose® CL-6B (Pharmacia) and Dyematrex™ Blue A (Amicon) represent preferred commercially-available examples of this type of group-specific adsorbent, although other triazinyl dye media capable of binding human diploid fibroblast or lymphoblastoid interferons are obvious equivalents. In the case of Blue Sepharose® CL-6B, the dye ligand (Cibacron® Blue F3G-A) is covalently attached to a cross-linked agarose gel (Sepharose® CL-6B) by a triazine coupling method disclosed by Bohme et al., *J. Chromatogr.* 69: 209 (1972).

The concentration of coupled dye in the final product is approximately 2 μmol/mL swollen gel. A partial structure of Blue Sepharose ® CL-6B, as disclosed by the manufacturer, is provided below:

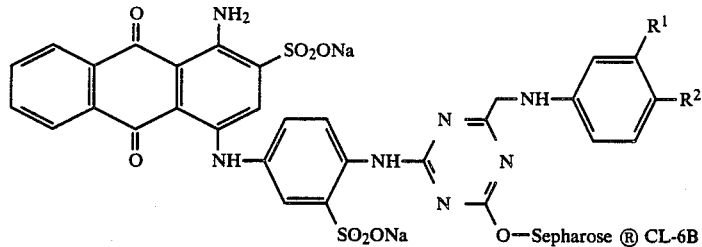

$R^1$ = H or $SO_2ONa$
$R^2$ = $SO_2ONa$ or H

The present invention, however, concerns that fraction of fibroblast or lymphoblastoid culture medium which passes unbound through an affinity column containing Blue Sepharose ® CL-6B. In a series of experiments in which this fraction was examined for residual biological activity, it was found that the unbound fraction contained substances capable of inhibiting growth of heterologous human cells. Moreover, the biological activity of these substances was distinct from that attributable to trace levels of interferons.

Preliminary characterization experiments have indicated the following:

(1) The growth-inhibiting activity exhibited by the unbound protein fraction is destroyed when this fraction is exposed to proteolytic enzymes, for example, trypsin, pronase or proteinase K.
(2) The growth-inhibiting activity is destroyed when the unbound protein fraction is heated to 100° C. for 2 min.
(3) The growth-inhibiting activity does not pass through a dialysis membrane.
(4) When the unbound fraction is sub-fractionated on the basis of molecular weight using a gel-filtration column, the sub-fraction containing proteins in the molecular weight range of 10,000 daltons to 80,000 daltons has growth-inhibiting activity.
(5) The growth-inhibiting activity is greatest for sub-fractions with molecular weights of about 12,000 daltons and about 60,000 daltons.
(6) The unbound protein fraction does not exhibit interferon activity.
(7) The growth-inhibiting activity of the unbound fraction can be observed when the fraction is added to culture media containing human lymphoblastoid (Namalva) cells which are insensitive to the activity of interferons.
(8) The unbound protein fraction also inhibits growth of mouse myeloma cells in vitro.

These results suggest that the growth-inhibiting substances are proteins with molecular weights of about 12,000 daltons and about 60,000 daltons. Further, these substances exhibit a biological activity distinct from interferons.

Additional experiments have indicated preferred cell lines for production of maximum amounts of the growth-inhibiting proteins. These cell lines, which are continuous human lymphoblastoid cells capable of growth in suspension culture, are known as the Daudi, Namalva, and Raji cell lines. These cell lines, upon induction with mezerein, secrete growth-inhibiting proteins at a rate sufficient to provide ten- to twenty-fold higher specific activities relative to previously studied human diploid fibroblast cells. However, treatment of human diploid fibroblast cells with (polyribo I:polyribo C) as described by Knight, Jr. (*Proc. Natl. Acad. Sci. USA* 73: 520 (1976)) produces growth-inhibiting proteins of the greatest stability and is thus preferred in some applications.

The American Type Culture Collection deposit accession numbers for these cell lines are listed below:

| Cell Line | Deposit Accession Number |
| --- | --- |
| Raji | ATCC CCL 86 |
| Daudi | ATCC CCL 213 |
| Namalva | ATCC CCL 1432 |

To assay the activity of the growth-inhibiting proteins, a sample of culture medium or other preparation to be tested is added to a population of growing Namalva cells. After 48 hours, the cells are counted with a hemocytometer. Optionally, DNA synthesis can be estimated by measuring cellular incorporation of radiolabeled thymidine. In these assays, one unit of activity is defined as the minimum concentration of growth-inhibiting protein capable of inhibiting cell growth or DNA synthesis by 50%.

Growth-inhibiting activities have been measured in crude culture supernatant fluids obtained by induction of Daudi, Namalva, and Raji cells. An activity of 2-4 units per mL was observed in culture supernatant fluids or Daudi and Namalva cells, and an activity of 5-16 units per mL in Raji cell supernatant fluids. Thus, Raji cells represent a preferred cell line for use with PMA or mezerein in the process of the present invention.

To induce secretion of the growth-inhibiting protein components, lymphoblastoid or other selected cells are grown, preferably in serum-free medium, to a density of about $1 \times 10^5$ cells/mL to about $1 \times 10^6$ cells/mL. Preferably, the cells are grown to a density of about $5 \times 10^5$ cells/mL. At this point, mezerein is added to growth medium to provide a concentration of about $1 \times 10^{-6}$M to about $1 \times 10^{-8}$M. Preferably, mezerein is added to medium to provide a concentration of about $1 \times 10^{-7}$M. Following 48 hours of growth at 37° C. in the presence of mezerein, the cells are collected by centrifugation, washed once with fresh growth medium (containing no mezerein or other inducer), and resuspended in fresh medium at a density of about $1 \times 10^6$ cells/mL. After an additional 48 hours at 37° C., the cells are again collected by centrifugation, and then discarded. The supernatant fluid, containing secreted proteins, represents a crude extract, which can be tested for activity or processed further. The volume of a crude extract can be reduced and its growth-inhibiting activity concentrated by lyophilization or ultrafiltration.

To achieve additional purification, a concentrated crude extract can be applied to a column containing a triazinyl dye ligand capable of binding human diploid fibroblast or lymphoblastoid interferons, for example a column containing Blue Sepharose ® CL-6B, and the unbound fraction collected and concentrated again. This unbound fraction can be applied to a gel filtration column and those sub-fractions containing cell growth-inhibiting activity can then be collected.

The process and products of the present invention are further illustrated by the following examples. In the examples, all temperatures are in degrees Celsius and all parts and percentages are by weight unless otherwise indicated.

EXAMPLE 1

Preparation by Lyophilization of Protein Fraction Containing Growth-Inhibiting Proteins from Human Diploid Fibroblast Cells Tissue culture supernatant fluid containing growth-inhibiting proteins and crude human diploid fibroblast interferon (IFN-$\beta$) was produced by growing human diploid fibroblast cells (neonatal foreskin fibroblasts, FS-4) in serum-free medium as described by Knight, Jr., *Proc. Natl. Acad. Sci. USA* 73: 520 (1976). Sixteen liters of supernatant fluid were adjusted to 1M NaCl and concentrated by ultrafiltration to a volume of approximately 300 mL. This concentrated supernatant fluid was applied to a 4 cm × 10 cm column containing Blue Sepharose ® CL-6B. The column packing had previously been equilibrated at about 23° with a solution containing 0.02M sodium phosphate (pH 7.2) and 1M sodium chloride. The column eluate, containing protein species unbound by dye ligand, was dialyzed against 0.001M tris(hydroxymethyl)aminomethane hydrochloride (Tris HCl), pH 7.2, at 4°, to remove sodium chloride. The resulting dialyzed column eluate was then lyophilized to dryness. This lyophilized material was dissolved in 4 mL of a serum-free growth medium, RPMI 1640 (GIBCO). Insoluble material was removed by centrifugation and soluble proteins were dialyzed against RPMI 1640 at 4°. The resulting material was then used directly for in vitro studies of growth inhibition.

EXAMPLE 2

Preparation by Ultrafiltration of Protein Fraction Containing Growth-Inhibiting Proteins from Human Diploid Fibroblast Cells Six liters of tissue culture supernatant fluid containing growth-inhibiting proteins and crude IFN-$\beta$ were concentrated to about 300 mL and applied to a column containing Blue Sepharose ® CL-6B, substantially as described in Example 1. The column eluate was concentrated to a volume of 3 mL using an anisotropic ultrafiltration membrane with a nominal molecular weight cutoff of 10,000 daltons (Amicon YM-10). The resulting concentrated extract was dialyzed against serum-free growth medium (RPMI 1640) at 4° and subsequently tested for growth-inhibiting activity.

EXAMPLE 3

Inhibition of Cell Growth and DNA Synthesis by Protein Fraction Containing Growth-Inhibiting Proteins This example demonstrates that the protein fraction produced by the present invention contains substances which inhibit growth of human lymphoblastoid cells in vitro. The protein preparation employed in these experiments was that described in Example 2, above, which contains both the 12,000 dalton and 60,000 dalton proteins.

The cell line selected for growth-inhibition studies was the Namalva lymphoblastoid cell line discussed above. Namalva cells are insensitive to the growth-inhibitory effect of interferons.

Cells were grown at 37° in a 5% $CO_2$/95% air incubator in RPMI 1640 medium supplemented with 10% fetal calf serum and the antibiotic gentamycin. Typically, cell numbers double every 24 hours.

In growth-inhibition experiments, cells were grown in 200 $\mu$l of the above-described medium in one well of a 96-well microtiter dish. Varying volumes (1 $\mu$L to 50 $\mu$L) of protein fraction to be tested for activity were added to wells containing test cells. Cells were counted in a hemocytometer 48 hours and 72 hours after addition of protein fraction. The fraction inhibited growth of Namalva cells at 50 to 400 mg protein/mL. Addition of sufficient fraction inhibited cell growth completely. One unit of growth inhibitory activity was defined as the lowest concentration (highest dilution) of proteins capable of providing a 50% inhibition of cell growth under the conditions of the assay described above.

To measure inhibition of DNA synthesis, cells were grown in the presence and absence of fraction containing growth-inhibiting proteins. After 24 hours, $^3$H-thymidine was added to provide a label concentration of 1 $\mu$C/mL. Cells were then incubated for an additional 5 hours at 37°, and then each cell suspension was transferred to glass fiber filters. The immobilized cells were washed twice with 5% trichloroacetic acid and finally washed twice with 95% ethanol. Radioactivity on filters was counted using a liquid scintillation counter. The resulting data indicated that cells grown in the presence of growth-inhibiting proteins had incorporated significantly less labeled thymidine. The apparent inhibition observed was proportional to the amount of growth-inhibiting proteins added.

Results of representative growth-inhibition experiments are set forth in the following table:

TABLE I

| Concentration of Protein Fraction Containing Growth-Inhibiting Proteins | Other Treatment | Inhibition of Cell Growth (%) | Inhibition of $^3$H—thymidine Incorporation (%) |
|---|---|---|---|
| 20-fold dilution | None | 70 | 95 |
| 10-fold dilution | None | 90 | 95 |
| 20-fold dilution | Excess anti-IFN-$\beta$ antibody added | 70 | — |
| None | 1000 units/mL IFN-$\beta$ added | 0 | — |
| 20-fold dilution | Proteinase K added | 10 | — |
| 20-fold dilution | Fraction held at 100° for 2 min. prior to assay | 15 | — |

Assays for IFN-$\beta$ in preparations containing growth-inhibiting proteins indicated the presence, at levels of about 500 to about 2000 units/mL concentrated extract, of IFN-$\beta$. However, control experiments indicated that growth of Namalva cells was unaffected by levels of IFN-β up to 2000 units/mL.

EXAMPLE 4

Inhibition of Growth of Heterologous Cell Types by Growth-Inhibiting Proteins Growth of other cell types is also inhibited by protein fractions prepared by the process of the present invention. Human WISH cells were grown in microtiter dishes from initial concentrations of 20,000 cells per well. Fraction prepared according to Example 1 containing growth-inhibiting proteins were added to growing cells. After two days, cells were treated with trypsin to detach them from wall surfaces for counting. Inhibition of cell growth was observed in cell populations to which growth-inhibiting proteins had been added. In substantially similar tests, growth-inhibiting proteins were also observed to inhibit growth of mouse myeloma cells, demonstrating that the activity of these proteins is not species-specific.

EXAMPLE 5

Determination of Molecular Weights of Growth-Inhibiting Proteins

To estimate the molecular weights of the growth-inhibiting proteins, a preparation, prepared as in Example 2, containing the partially purified unbound protein fraction was applied to a 0.5 cm×50 cm column containing Sephadex® G-75, which had been previously equilibrated with 20 mM sodium phosphate buffer, pH 7.2, 0.15M NaCl at 4°. 1.0 mL aliquots were collected. Following dialysis against RPMI 1640 medium, each aliquot was assayed for growth-inhibiting activity. Aliquots 10-12, which exhibited significant growth-inhibiting activity, constitute a 60,000 dalton sub-fraction of the unbound protein fraction. Aliquots 18-20, which also exhibited growth-inhibiting activity, constitute a 12,000 dalton sub-fraction of the unbound protein fraction.

EXAMPLE 6

Determination of Growth Inhibitory Activities of Proteins with Molecular Weights of 60,000 and 12,000 Daltons Sub-fractions eluted from the Sephadex® G-75 column were assayed for growth inhibitory activity. Sub-fractions containing proteins with molecular weights of about 60,000 and about 12,000 daltons exhibited the highest growth inhibitory activity.

What is claimed is:

1. A process for preparing a protein fraction comprising proteins which are capable of inhibiting the growth of human lymphoblastoid cells, said process comprising:
   (a) growing either (1) human diploid fibroblast cells in a culture medium containing a mixture of polyinosinic and polycytidylic acids or (2) human lymphoblastoid cells selected from the group consisting of Raji, Daudi and Namalva cells in a culture medium containing either mezerein or phorbol 12-myristate 13-acetate (PMA) under conditions which induce the cells to secrete proteins into culture medium;
   (b) contacting the culture medium with an immobilized triazinyl dye capable of binding human fibroblast or lymphoblastoid interferons, whereby bound and unbound protein fractions are formed; and
   (c) isolating the unbound fraction which contains the growth-inhibiting proteins.

2. A process according to claim 1 wherein the immobilized triazinyl dye is a compound of the formula

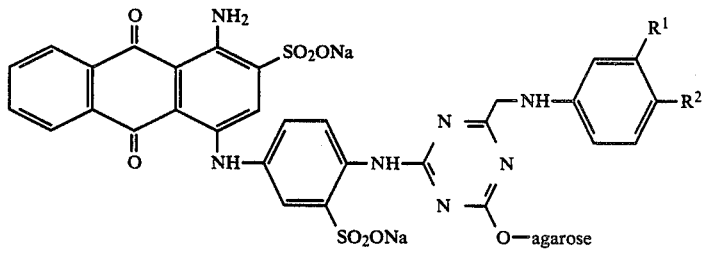

wherein
R¹=H or SO₂ONa
R²=SO₂ONa or H.

3. A process according to claim 2, wherein the cells grown in step (a) are humam lymphoblastoid cells selected from the group consisting of Raji, Daudi and Namalva cells.

4. A process according to claim 3, wherein conditions which induce the human lymphoblastoid cells to secrete proteins into the culture medium are established by:
   (a) growing the cells to a density of about $1\times 10^5$ cell per mL to about $1\times 10^6$ cells per mL;
   (b) contacting the cells with an inducer selected from the group consisting of mezerein and phorbol 12-myristate 13-acetate, at a concentration of about $1\times 10^{-6}$M to about $1\times 10^{-8}$M, for a period of about 24 hours to about 72 hours;
   (c) collecting the cells by centrifugation and washing the cells with inducer-free culture media; and
   (d) resuspending the cells in inducer-free culture media at a density of about $5\times 10^5$ cells per mL to about $5\times 10^6$ cells per mL.

5. A process according to claim 4, wherein the culture medium is serum-free medium.

6. A process according to claim 5, wherein the cells are Raji cells, having ATCC deposit accession number ATCC CCL 86.

7. A process according to claim 6, wherein the inducer added to culture medium is mezerein.

8. A process according to claim 7, wherein the concentration of mezerein in the culture medium is about $5\times 10^{-6}$M to about $5\times 10^{-7}$M.

9. A process according to claim 2 wherein human diploid fibroblast cells are grown in a culture medium containing a mixture of polyinosinic and polycytidylic acids.

10. A process according to claim 1 further comprising: (d) isolating from the unbound fraction, a sub-fraction containing proteins of about 12,000 daltons or a sub-fraction of about 60,000 daltons.

11. A protein fraction comprising a growth-inhibiting protein exhibiting an apparent molecular weight by gel filtration of about 12,000 daltons and capable of inhibiting growth of human lymphoblastoid cells, said protein fraction having been prepared by a process according to claim 1.

12. A protein fraction comprising a growth-inhibiting protein exhibiting an apparent molecular weight by gel filtration of about 60,000 daltons and capable of inhibiting growth of human lymphoblastoid cells, said protein fraction having been prepared by a process according to claim 1.

* * * * *